(12) United States Patent
Montgomery, Jr.

(10) Patent No.: US 7,136,696 B2
(45) Date of Patent: Nov. 14, 2006

(54) NEURON SIGNAL ANALYSIS SYSTEM AND METHOD

(75) Inventor: Erwin B. Montgomery, Jr., Cleveland Heights, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 666 days.

(21) Appl. No.: 10/138,987

(22) Filed: May 3, 2002

(65) Prior Publication Data

US 2003/0191408 A1    Oct. 9, 2003

Related U.S. Application Data

(60) Provisional application No. 60/370,123, filed on Apr. 5, 2002.

(51) Int. Cl.
*A61B 5/04*    (2006.01)

(52) U.S. Cl. ...................... 600/544; 600/545

(58) Field of Classification Search .............. 600/544, 600/545, 547, 554
See application file for complete search history.

(56) References Cited

U.S. PATENT DOCUMENTS

| | | | |
|---|---|---|---|
| 3,826,244 A | 7/1974 | Salcman et al. | |
| 3,841,310 A | 10/1974 | Goldstein | |
| 4,245,645 A | 1/1981 | Arseneault et al. | |
| 4,461,304 A | 7/1984 | Kuperstein | |
| 5,081,990 A | 1/1992 | Deletis | |
| 5,119,832 A | 6/1992 | Xavier | |
| 5,143,067 A | 9/1992 | Rise et al. | |
| 5,165,412 A * | 11/1992 | Okazaki | 600/439 |
| 5,375,594 A | 12/1994 | Cueva | |
| 5,458,631 A | 10/1995 | Xavier | |
| 5,563,067 A | 10/1996 | Sugihara et al. | |
| 5,701,909 A | 12/1997 | Amir et al. | |
| 5,743,860 A * | 4/1998 | Hively et al. | 600/544 |
| 5,902,236 A | 5/1999 | Iversen | |
| 6,011,996 A | 1/2000 | Gielen et al. | |
| 6,055,452 A | 4/2000 | Pearlman | |
| 6,157,861 A | 12/2000 | Faltys et al. | |
| 6,175,753 B1 | 1/2001 | Menkes et al. | |
| 6,201,982 B1 | 3/2001 | Menkes et al. | |
| 6,282,437 B1 | 8/2001 | Franck et al. | |
| 6,298,262 B1 | 10/2001 | Franck et al. | |
| 6,301,492 B1 | 10/2001 | Zonenshayn | |
| 6,308,097 B1 | 10/2001 | Pearlman | |

(Continued)

FOREIGN PATENT DOCUMENTS

EP    1062973 A1    12/2000

(Continued)

OTHER PUBLICATIONS

Analysis of Single Unit Firing Patterns in Multi-Unit Intrafascicular Recordings. Eleanor Goodall, Kenneth Horch and Timothy McNaughton. 2200 Medical & Biological Engineering & Computing. May 31, 1993, No. 3, Stevenage, Herts., GB . pp. 257-267.

(Continued)

*Primary Examiner*—Max F. Hindenburg
*Assistant Examiner*—Rene Towa
(74) *Attorney, Agent, or Firm*—Calfee, Halter & Griswold LLP

(57) ABSTRACT

Electrical signal data from a target location are recorded and collected. A signal analyzer analyzes the signal data and determines whether characteristics of the signal data resemble noise data or whether a departure from noise is present. If the characteristics show a departure from noise, neuronal activity at the target location is indicated.

44 Claims, 7 Drawing Sheets

U.S. PATENT DOCUMENTS

| | | | |
|---|---|---|---|
| 6,330,466 B1 * | 12/2001 | Hofmann et al. | 600/378 |
| 6,343,226 B1 | 1/2002 | Sunde et al. | |
| 6,421,559 B1 | 7/2002 | Pearlman | |
| 6,428,484 B1 | 8/2002 | Battmer et al. | |
| 6,470,226 B1 | 10/2002 | Olesen et al. | |
| 6,493,576 B1 | 12/2002 | Dankwart-Eder | |
| 6,507,754 B1 * | 1/2003 | Le Van Quyen et al. | 600/544 |
| 6,529,765 B1 | 3/2003 | Franck et al. | |
| 6,546,277 B1 | 4/2003 | Franck et al. | |
| 6,600,943 B1 | 7/2003 | Kiuchi et al. | |
| 6,622,035 B1 | 9/2003 | Merilainen et al. | |
| 2001/0014820 A1 | 8/2001 | Gielen et al. | |
| 2001/0016765 A1 | 8/2001 | Gielen et al. | |
| 2001/0027271 A1 | 10/2001 | Franck et al. | |
| 2001/0027336 A1 | 10/2001 | Gielen et al. | |
| 2001/0053885 A1 * | 12/2001 | Gielen et al. | 604/20 |
| 2002/0022872 A1 | 2/2002 | Gielen et al. | |
| 2002/0026123 A1 | 2/2002 | Pearlman | |
| 2002/0095194 A1 | 7/2002 | Charvin et al. | |
| 2002/0113607 A1 | 8/2002 | Yukimasa | |
| 2002/0188330 A1 * | 12/2002 | Gielen et al. | 607/45 |
| 2003/0009112 A1 | 1/2003 | Hammerle et al. | |
| 2003/0032001 A1 | 2/2003 | Broderick et al. | |
| 2003/0083724 A1 | 5/2003 | Jog et al. | |
| 2003/0105410 A1 | 6/2003 | Pearlman | |
| 2003/0111343 A1 | 6/2003 | Oka et al. | |
| 2003/0176905 A1 | 9/2003 | Nicolelis et al. | |
| 2003/0187351 A1 | 10/2003 | Franck et al. | |

FOREIGN PATENT DOCUMENTS

| | | |
|---|---|---|
| EP | 1240876 A1 | 9/2002 |
| EP | 0689051 B1 | 11/2002 |
| EP | 0892654 B1 | 6/2003 |
| FR | 2 803 186 A1 | 1/2001 |
| FR | 2803186 | 7/2001 |
| WO | WO 94/22365 | 10/1994 |
| WO | WO 96/12439 | 5/1996 |
| WO | WO 97/37720 | 10/1997 |
| WO | WO 97/48447 | 12/1997 |
| WO | WO 99/36122 | 7/1999 |
| WO | WO 03/028521 A2 | 4/2003 |
| WO | WO 03/077988 A1 | 9/2003 |

OTHER PUBLICATIONS

W. Wiemer; D. Kaack; P. Kezdi; H. Klatt, "Peak Discrimination as a Method for Quantitative Evaluation of Neural Activity by Computer," Medical and Biological Engineering, May 1995, pp. 337-357.

William Cobb; Cristoforo Morocutti, "The Evoked Potentials," Electroencephalography and Clinical Neurophysiology, Supplement No. 26, 1967, pp. 7-11.

George L. Gerstein; Donald H. Perkel; K.N. Subramanian, "Identification of Functionally Related Neural Assemblies," Brain Research, Elsevier/North-Holland Biomedical Press, 1978, pp. 43-62.

Jose C. Principe; Jack R. Smith, "Automatic Recognition of Spike and Wave Bursts," Elsevier Science Pubnlishers B.V. (Biomedical Division), 1985 pp. 115-132.

Eric L. Schwartz; Alexis Ramos; E. Roy John, "Single Cell Activity in Chronic Unit Recording: A Quantitative Study of the Unit Amplitude Spectrum," Brain Research Bulletin, vol. 1, pp. 57-68.

Masafumi Yoshida; Hitoshi Mizuki; Akihiro Nagase; Shigeki Kuga; Morihisa Shira-Hama; Mitsuo Watanabe; Shinken Kuramoto, "Microcomputer Mapping," Department of neurospurgery, Kurume University School of Medicine, 1981, pp. 719-728.

* cited by examiner

NEURON SIGNAL ANALYSIS SYSTEM AND METHOD

RELATED APPLICATION

This application claims priority to provisional U.S. Application Ser. No.: 60/370,123, filed Apr. 5, 2002.

FIELD OF THE INVENTION

The present invention relates to the neuron signal analysis arts. It finds particular application to a system and method for analyzing signal data.

BACKGROUND OF THE INVENTION

Deep brain stimulation (DBS) employs high-frequency stimulation to stimulate a targeted region of the brain. It includes a surgical procedure where one or more electrodes are positioned and placed into one of several possible targets in the brain. The electrode is then connected to an impulse generator that is implanted subcutaneously, in a manner similar to that used for a pacemaker. Stimulation parameters are adjusted to maximize therapeutic effects. Deep brain stimulation is, for example, a surgical treatment for Parkinson's disease.

In this procedure and other similar procedures, the stimulation electrode works effectively only if positioned near neurons that are targeted for stimulation. To properly position the electrode, a recording microelectrode is used to record electrical signals from within the brain or other tissue. From these signals, a surgeon or other expert must identify and isolate extracellular action potentials of individual neurons. If the action potentials are properly identified, the location of the targeted neurons is more than likely determined.

There are various techniques for isolating neuron cell discharges from electrical signal data. However, the prior techniques depend on the subjective judgment of an expert that attempts to distinguish a nerve cell discharge from a large quantity of noise signals. This is performed, for example, by viewing an oscilloscope and analyzing a tracing of the recorded electrical activity. Alternately, the electrical signal data is made audible and the expert listens for certain characteristics that may represent neuron cell discharges. In either case, experts must be highly trained and sophisticated in order to analyze the electrical signal data. They typically have extensive prior knowledge of what a nerve cell discharge looks like and/or sounds like as opposed to an artifact signal.

Due to its subjective nature, this is a tedious and error prone process. Furthermore, the limited number of qualified experts hinders the ability to perform procedures that require identification of neurons.

The present invention provides a new and useful system and method of analyzing electrical signals that addresses one or more of the above problems.

BRIEF SUMMARY OF THE INVENTION

In accordance with one embodiment of the invention, a system of positioning a microelectrode within a tissue is provided. The system comprises a microelectrode for collecting electrical signals, and a distribution logic that generates a statistical distribution of the electrical signals. An identification logic identifies whether the statistical distribution resembles a noise distribution, and a position controller controls the position of microelectrode. The position controller moves or does not move the electrode based on the identification of the statistical distribution.

In accordance with another embodiment of the invention, a software product for analyzing electrical signal data collected from tissue is provided. The software includes first computer executable instructions that cause a computer to generate a statistical distribution of the electrical signal data. It further includes second computer executable instructions that cause a computer to analyze the statistical distribution and indicate whether neuronal activity is present in the electrical signal data based on a shape of the statistical distribution.

In accordance with another embodiment of the invention, a method of determining a nerve discharge from a plurality of electrical signals is provided. At least one characteristic of the plurality of electrical signals is statistically analyzed and a distribution curve is generated from at least one characteristic. A statistical characteristic of the distribution curve is determined. Whether at least one nerve discharge signal occurs within the electrical signal data is then determined based on the statistical characteristic of the distribution curve.

BRIEF DESCRIPTION OF THE DRAWINGS

In the accompanying drawings which are incorporated in and constitute a part of the specification, embodiments of the invention are illustrated which, together with a general description of the invention given above and the detailed description given below, serve to example the principles of this invention.

DETAILED DESCRIPTION OF THE INVENTION

The invention may be embodied in various forms. The following includes definitions of exemplary terms used throughout the disclosure. Both singular and plural forms of all terms fall within each meaning:

"Logic", as used herein, includes but is not limited to hardware, firmware, software and/or combinations of each to perform a function(s) or an action(s). For example, based on a desired application or needs, logic may include a software controlled microprocessor, discrete logic such as an application specific integrated circuit (ASIC), or other programmed logic device. Logic may also be fully embodied as software.

"Signal", as used herein, includes but is not limited to one or more electrical signals, analog or digital signals, one or more computer instructions, a bit or bit stream, or the like.

"Software", as used herein, includes but is not limited to one or more computer executable instructions, routines, algorithms, modules or programs including separate applications or code from dynamically linked libraries for performing functions and actions as described herein. Software may also be implemented in various forms such as a stand-alone program, a servlet, an applet, instructions stored in a memory, part of an operating system or other type of executable instructions. It will be appreciated by one of ordinary skill in the art that the form of software is dependent on, for example, requirements of a desired application, the environment it runs on, and/or the desires of a designer/programmer or the like. Articles of manufacture may embody software such as computer readable media including magnetic, digital or optical storage devices, and electronic memory devices and circuits.

As will be described in greater detail below, the various embodiments of the invention provide for automatically advancing microelectrodes and determining when a neuronal action potential has been encountered as distinct from background electrical noise. Decisions as to whether a neuronal action potential is present does not depend on an operator's subjective judgment based on visual or auditory inspection. Rather, the system can objectively determine the presence of neuron activity within a collected set of signal data based on analyzing statistical characteristics of the signal data. For exemplary purposes, the discussion is based on recording signal data from brain tissue; however, it will readily apply to other types of tissues and signals.

Figure 1:
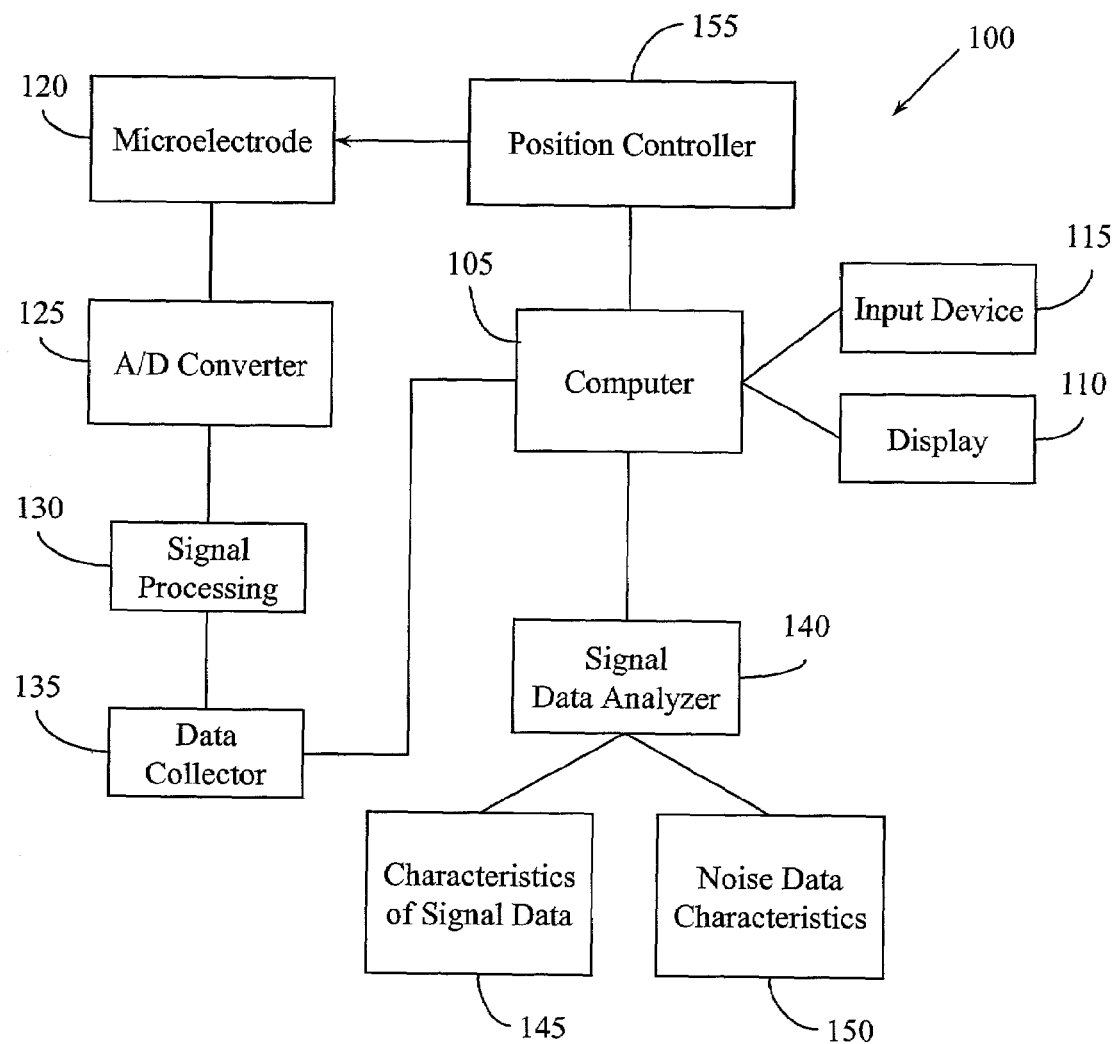
FIG. 1 is an exemplary system diagram in accordance with one embodiment of the present invention.

Illustrated in FIG. 1 is one embodiment of a system 100 for positioning a microelectrode and analyzing electrical signal data. For exemplary purposes, the system will be described for use with a brain tissue and identification of neurons within the brain tissue. The system 100 is controlled by a computer 105 that may be a dedicated system, a general purpose computer, multiple computers, a computer connected to a network or other structural configuration as may be desired. Information from the computer 105 is displayed on a display 110. An operator may input data and/or instructions to the computer 105 using an input device 115 such as a keyboard, mouse, pointer, touch screen, microphone and/or any other known input device.

A microelectrode 120, once implanted into a subject, records electrical activity therein. The microelectrode 120 is implanted near a target position within the brain and records electrical signals for a predetermined time period, for example, 1/10 of a second or any other desired time period. An analog-to-digital converter 125 converts the recorded signals into digital signal data. Optional signal processing 130 may be performed such as filtering, amplification and other desired effects. The recorded data signals are collected and stored by a data collector 135 that stores the signal data in one or more data arrays, data bases, files, or other data structures for further processing by the computer 105.

With further reference to FIG. 1, the electrical signal data is then analyzed by a signal data analyzer 140 that determines whether the signal data is noise or whether it contains neuron discharge signals. In this embodiment, the analyzer 140 is embodied as software. The analysis is based on the observation that electrical noise in the signal data is over-represented compared to the relatively infrequent occurrence of a neuronal action potential. In other words, noise signals dominate the signal data whether or not a neuron discharge is present. So in this embodiment, the analysis focuses on examining the noise characteristics 145 of the signal data, and logic of the signal analyzer 140 determines the extent to which the signal data resembles exemplary noise data characteristics 150.

If the signal data resembles noise, the analyzer 140 sets a flag, generates an instruction or other type of signal which causes a position controller 155 to move the microelectrode 120 to a new selected location. The position controller 155 controls the position of the microelectrode 120 based on the analyzed characteristics of the signal data. The position controller 155 may be a hydrolytic drive that advances or retracts the microelectrode. Of course, other types of drive mechanisms can be used. The microelectrode 120 then records a new set of signal data and the process repeats until a location that contains neuron discharge signals is found or the process is stopped by an operator.

If the signal characteristics show a statistical departure from exemplary noise data, then the signal data is judged to contain one or more neuron discharge signals. That is because the presence of neuron discharge signals will cause the departure. How much of a departure is needed before triggering an indication of neuron activity can be set by a threshold. When the departure is great enough to pass the threshold, it is determined that neural activity is present. In this manner, an objective analysis is made rather than a subjective determination from an operator.

Figure 2:
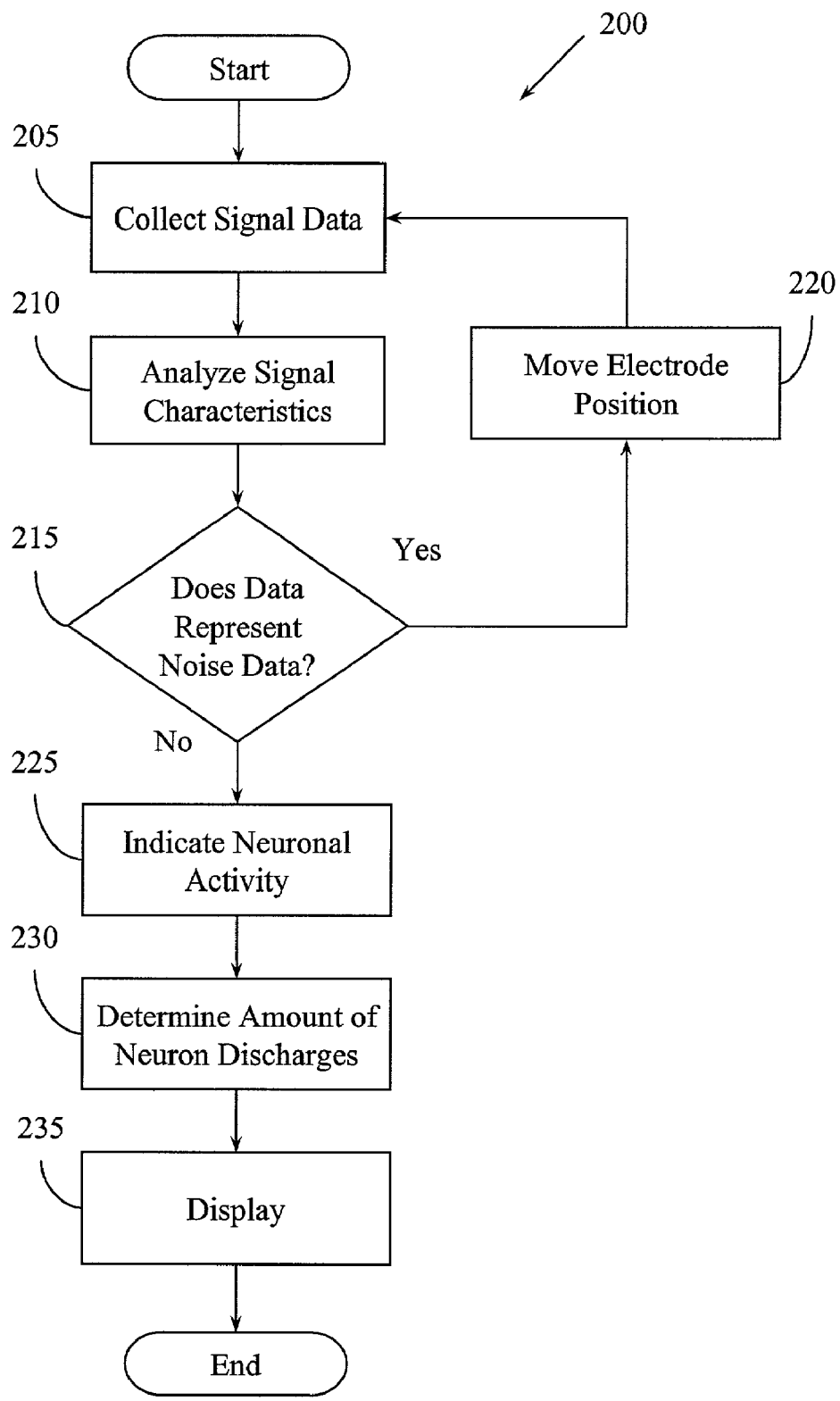
FIG. 2 is an exemplary methodology of determining neuronal activity in accordance with one embodiment of the present invention.

Illustrated in FIG. 2 is an exemplary methodology 200 of the system shown in FIG. 1 for collecting signal data and determining whether neuronal activity is present. The rectangular elements denote "processing blocks" and represent computer software instructions or groups of instructions. The diamond shaped elements denote "decision blocks" and represent computer software instructions or groups of instructions which affect the execution of the computer software instructions represented by the processing blocks. Alternatively, the processing and decision blocks represent steps, functions, and/or actions performed by functionally equivalent circuits such as a digital signal processor circuit, an application specific integrated circuit (ASIC) or microprocessor. The diagram does not depict syntax of any particular programming language. Rather, the diagram illustrates the functional information one skilled in the art requires to fabricate circuits or to generate computer software to perform the processing of the system.

It will be appreciated that electronic and software applications involve dynamic and flexible processes such that the illustrated blocks can be performed in other sequences different than the one shown. It will also be appreciated by one of ordinary skill in the art that elements embodied as software may be implemented using various programming approaches such as machine language, procedural, object oriented or artificial intelligence techniques. It should be noted that many routine program elements, such as initialization of loops and variables and the use of temporary variables are not shown. The above characterization also applies to the other figures showing methodologies, flow charts or processes.

With reference to FIG. 2, the process begins by collecting signal data (block 205) after a recording device, such as a microelectrode, is inserted at a target location within the brain or other tissue. Signals are recorded for a selected time period to obtain a set of electrical signal data. Characteristics of the signal data are then analyzed to determine whether it resembles noise data (block 210). For example, a statistical analysis of one or more characteristics of the signal data are performed and compared to noise data characteristics. A decision is made as to whether the signal data represents noise (block 215.) If it does, meaning that a neuron action potential has not been found, the microelectrode position is automatically moved to a new position (block 220) and the process repeats. If it does not resemble noise data to a predetermined level, neuronal activity is indicated to be contained in the signal data (block 225). In this manner, the position of microelectrode can be automatically controlled based on the analyzed signal characteristics.

For example, if a statistical characteristic of the signal data reflects a departure from what is expected from the same statistical characteristic of typical noise data, then neuron discharges are present. One possible statistical characteristic includes comparing a range of voltages from the signals. Other statistical characteristics, as will be described in greater detail below, may include a shape of a signal distribution curve, the size of tails from the distribution curve, a kurtosis value from the distribution curve, other desired characteristics, or a combination of these. Optionally, an amount of neuron discharges can be determined based on the amount of departure determined (block 230). As the departure from noise data increases, then the amount of neuron discharges present in the signal data is indicated to be greater. The statistical analysis and/or the results found can be displayed to an operator (block 235) for additional verification if desired.

Figure 3:
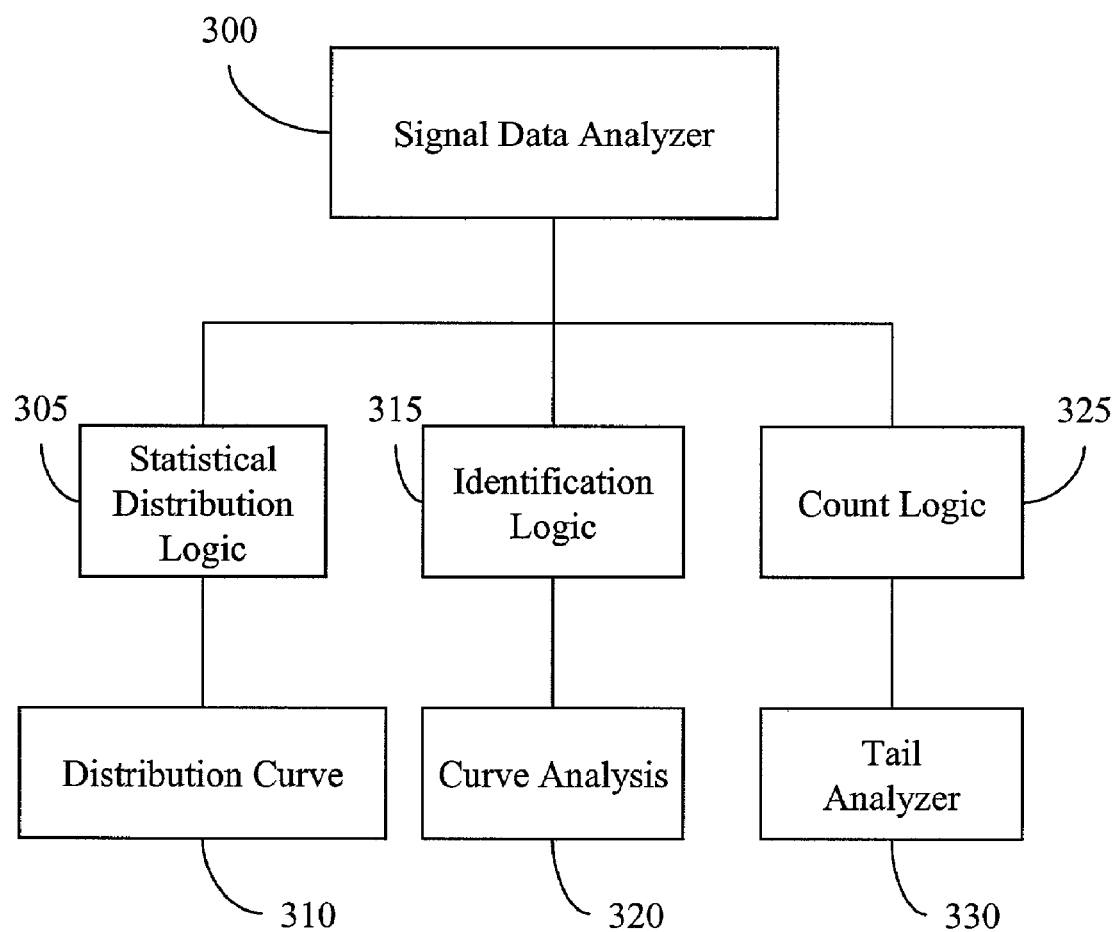
FIG. 3 is an another embodiment of the signal data analyzer shown in FIG. 1.

Illustrated in FIG. 3 is another embodiment of the signal data analyzer 140 shown as analyzer 300. The analyzer 300 is programmed to analyze signal characteristics of the signal data using statistical analysis. It should be noted that although the elements of the analyzer 300 are shown as separate elements, one or more of them may be embodied together as part of the same software program. The elements can also be embodied such that they are called by the analyzer 300 when desired. Of course, software can be structured in many ways depending on the preferences of the designer/programmer.

Figure 4:
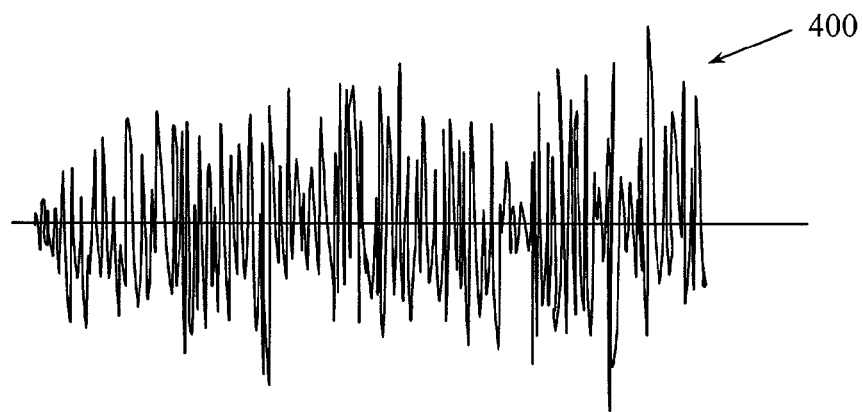
FIG. 4 is an exemplary tracing of electrical activity.
Figure 5:
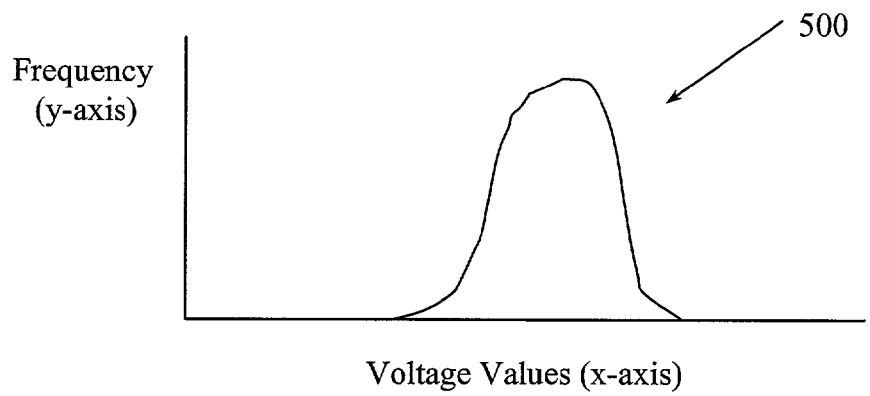
FIG. 5 is an exemplary statistical distribution curve of noise data based on voltage amplitudes.

As seen in FIG. 3, a statistical distribution logic 305 generates a statistical distribution curve 310 from the signal data based on one or more selected characteristics. In this embodiment, voltage amplitude values of each recorded signal are used. FIG. 4 illustrates an exemplary signal data 400 that may be seen on an oscilloscope tracing of electrical activity. FIG. 5 illustrates an exemplary noise distribution curve 500 of voltage amplitude values, for example, as a histogram showing frequency of occurrences (y-axis) of each voltage amplitude value (x-axis). Since electrical noise is over-represented in signal data, the statistical distribution of signal amplitudes will be normally and narrowly distributed. Thus, distribution curve 500 of noise data is a normal distribution curve generally characterized as bell-shaped with a lesser degree of variance from the mean, in other words with shorter tails.

If the distribution curve 310 of the current signal data resembles the noise distribution curve 500, then the signal data is determined to be noise without a neuron action potential. However, even when a neuronal signal is present in the signal data, the distribution curve 310 may appear normal or bell-shaped because neuron action potentials are relatively rare. But, the variance from the mean will be greater and the tails of the curve will be longer than that of a typical noise distribution curve 500, and these characteristics can be used to identify if a neuron action potential is present. To assist in identifying such differences from the noise distribution curve, further processing of the distribution curve 310 may be performed to exaggerate the distribution values from the mean. For example, logic can be included to determine the 4th order moment about the mean (4MOM) for the signal data. Of course, other orders such as 3rd, 5th, or other order can be used.

Figure 6:
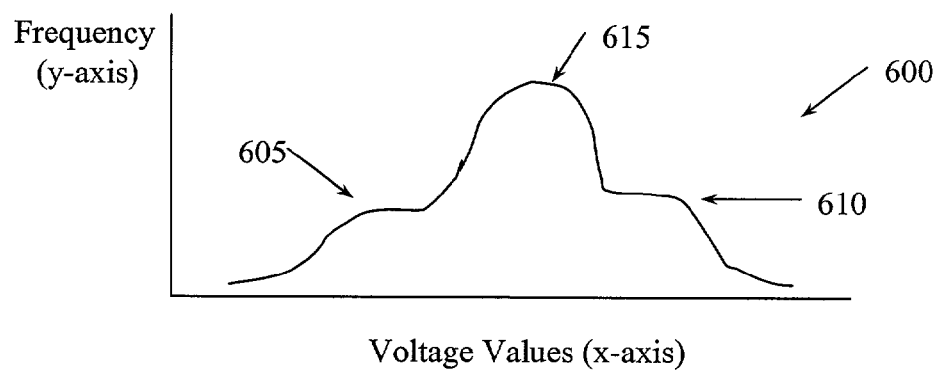
FIG. 6 is an exemplary statistical distribution curve of noise data that contains neuron discharge signals.

A distribution curve that represents noise with neuron discharge signals present may look like distribution curve 600 shown in FIG. 6. To better illustrate differences from the noise distribution curve 500, the curve 600 is shown with exaggerated values in its tail regions which may be obtained, for example, by applying a 4th order moment about the mean. The curve 600 shows a greater number of voltage occurrences 605, 610 in the tail regions beyond a central curve 615 as compared to the noise distribution curve 500. The central curve 615 represents the greatest concentration of values (e.g. noise signals). Furthermore, the tails are lengthened as compared to the exemplary noise distribution curve 500 indicating a greater range of voltages in the signal data. The signal analyzer 300 will consider curve 600 as a departure from the generally bell-shaped noise curve 500 at least in part due to the longer tails. The signal analyzer 300 can determine if a neuron action potential is present by determining if the distribution curve resembles noise data (e.g., noise distribution curve 500) or if it is a departure from noise data (e.g., distribution curve 600), the latter meaning neuron discharge signals are present. It will be noted that a distribution curve generated from signal data containing both noise and neuron discharge signals, like curve 600, will also resemble a bell-shaped curve. They differ from the "generally bell-shaped" noise curve 500 in their degree of kurtosis or width of distribution as will be described in greater detail below.

With further reference to FIG. 3, an identification logic 315 analyzes the distribution curve 310 generated from the current signal data. The logic 315 performs a curve analysis 320 to determines what type of curve it most likely is. In particular, it determines whether the curve 310 resembles a generally bell-shaped curve of noise data (e.g. FIG. 5). There are different ways to perform the curve analysis. For example, the shape of the curve can be compared to the shape of a noise distribution curve. In another embodiment, a central tendency value can be computed and then dispersions from the central tendency are measured. If a pre-selected amount of dispersions exists, then it is determined that neuron discharges are present.

In another embodiment, a kurtosis value is determined for the distribution curve. Kurtosis provides information about a curve's shape and, in particular, is based on the size of a distribution's tails. The larger the tails, the lower the kurtosis value. Thus, a generally normal distribution curve (representing only noise) will have smaller tails and a larger kurtosis value than a distribution curve with neuron discharges which will have larger tails. A threshold kurtosis value can be set such that if the kurtosis value of a distribution curve falls below the threshold, the analysis determines that one or more neuron discharges are present.

An exemplary equation for determining kurtosis is shown in Equation (1) below. In the equation, x is a current value from the signal data, $\mu$ is the mean of the data, N is the number of values in the data, $\sigma$ is the standard deviation. Of course, the kurtosis can be determined differently and/or with different variations of Equation (1). For example, the subtraction of "3" can be optional.

$$\text{Kurtosis} = \frac{\sum (x - \mu)^4}{N\sigma^4} - 3 \qquad (1)$$

With further reference to FIG. 3, a count logic 325 can be included to determine a relative amount of neuron discharge signals once it is determined that they are present. In one embodiment, the count logic 325 includes a tail analysis logic 330 that analyzes the tails of the distribution curve. Generally, as mentioned previously, larger tails indicate greater neuron activity. A number of occurrences beyond a selected threshold (e.g., beyond the 4th order moment about the mean) can indicate a quantity of neuron activity. Also, the kurtosis value can be used for this analysis. Again, the lower the kurtosis value, the larger the tails are, meaning, a greater amount of neuron discharges are present.

The amount of neuron signal firings can also be found by Equation 2. The number of voltage values recorded is represented by n, $(x-\mu)$ is the difference between each voltage point (x) and the average voltage ($\mu$) found in the signal data. This value is raised to the 4th power to exagerate its distance from the mean.

$$\text{Firings} = \frac{1}{n}\sum_{i=0}^{n-1}(x_i - \mu)^4 \qquad (2)$$

Figure 7:
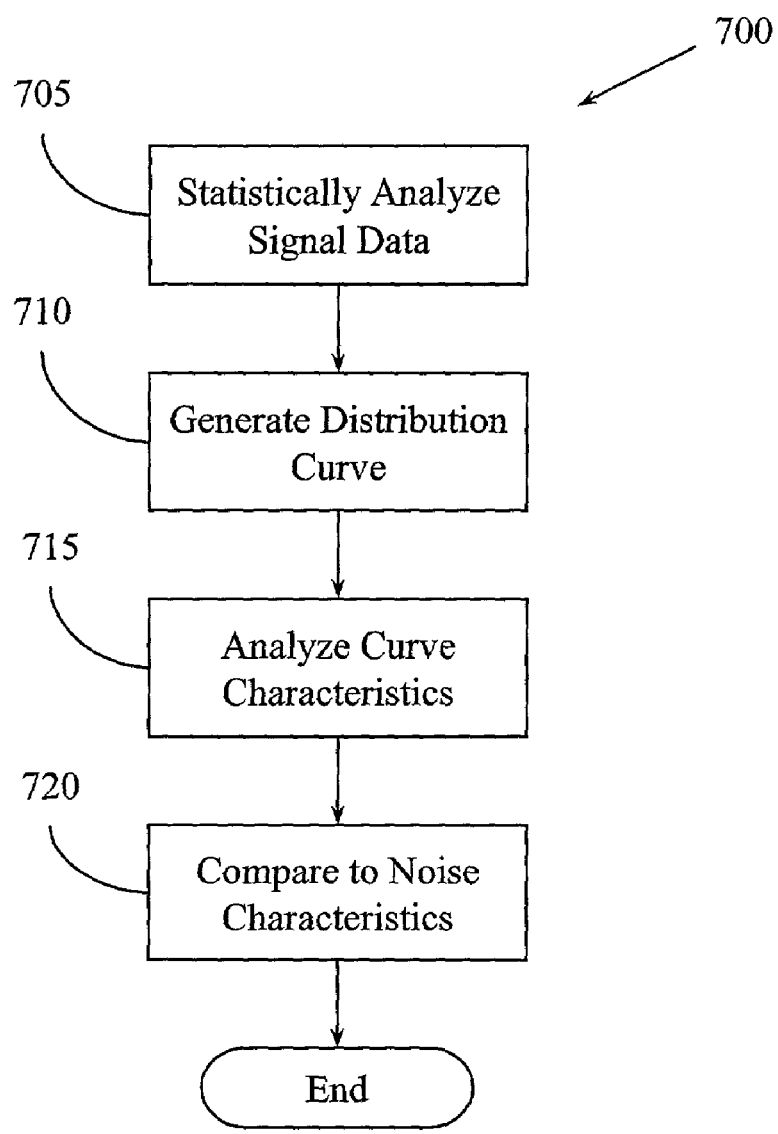
FIG. 7 is another exemplary methodology of analyzing signal data.

With reference to FIG. 7, an exemplary methodology 700 is shown for the signal data analyzer 300. The illustrated blocks may also represent an embodiment of the "analyze signal characteristics" block 210 from FIG. 2. After a set of signal data is collected, it is statistically analyzed (block 705). For example, a characteristic is selected, such as voltage amplitude values for each signal, and a distribution is generated using the selected values (block 710). Characteristics from the curve are then analyzed (block 715). For example, the curve's shape is determined and compared to a normal noise distribution curve (block 720). A kurtosis value can be determined which indicates the size of the distribution's tails. If the distribution resembles a noise distribution (e.g., by shape or by kurtosis value or by both), then it is judged to be noise data. If the distribution departs from a noise distribution, then it is judged to contain a neuron action potential. The results of the distribution or comparison, or both can be displayed for additional verification from a physician or other expert if desired.

Figure 8:
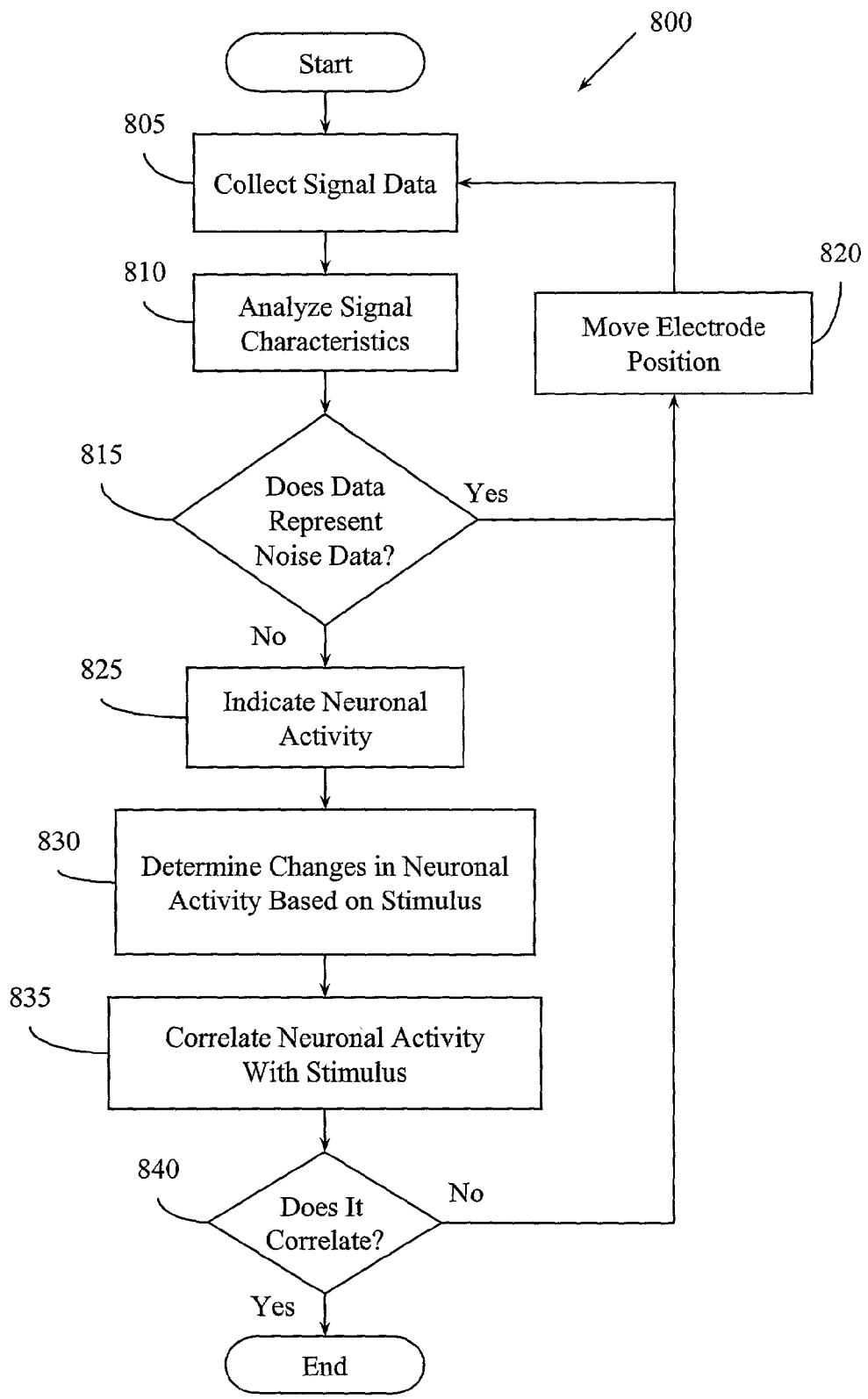
FIG. 8 is an exemplary methodology of correlating neuronal activity with an applied stimulus in accordance with another embodiment of the invention.

Illustrated in FIG. 8 is another exemplary methodology 800 used by the above systems for the identification of sensor-motor regions within an anatomical target. A sensori-motor region is identified by correlating neuronal activity changes (increases or decreases) temporally correlated with sensory stimulation or movement. The system automatically determines whether such a correlation exists and if so, whether the microelectrode is in the sensori-motor regions. In this embodiment, the signal data analyzer 140 and/or 300 includes or calls a correlation logic to perform the correlation as described below.

When the microelectrode is at a target position in the brain and neuronal activity is determined by the present system, a physician may wish to determine if that target position corresponds to a particular part of the patient such as the left hand. By stimulating or moving the left hand, or both, the system can record electrical activity at the target position and determine whether the stimulation triggers neuronal activity. The system generates a distribution curve for the recorded signal data as described above and, by analyzing changes in the distribution curve as a stimulus is applied, it can determine if there is a correlation. A more detail discussion follows with reference to FIG. 8.

As seen in FIG. 8, microelectrode signals are recorded for a brief epoch, for example 20 msec or other selected time period (block 805). The signals are statistically analyzed in a manner described above (block 810). A distribution is generated and the analysis determines whether it resembles noise data or whether a departure exists indicating the presence of neuronal activity (block 815). To assist the determination, the 4th order moment about the mean (4MOM) is determined of the signal data. If it resembles noise, the electrode position is moved (block 820) and the process repeats until a location is found that contains neuronal activity.

When neuronal activity is found at a target location (block 825), the physician can attempt to correlate the location with an area of the patient. A stimulus is applied and removed to an area, such as an arm or leg, and a plurality of signal data is recorded for a number of epochs. Between each epoch, data from sensory stimulation or movement is obtained. A buffer of these data (sensory, movement and the 4MOM) are recorded, for example, for 100 epochs or other selected quantity. This buffer contains the time course of neuronal activity (time course of the 4MOM) and sensory and/or movement. The time course of the 4MOM is correlated with the sensory and/or movement data. The results of the correlation are displayed so that the physician or electrophysiologist can see the correlation found that determines whether the neuronal activity is correlated with sensory and/or motor function and therefore, the microelectrode tip is within the sensori-motor region of the anatomical target.

A variety of sensory stimulations can be used. These include (but are not limited to) light touch, proprioception (joint capsule receptors) and muscle spindles. Correlation of neuronal activity to specific types of sensory stimulation have implications for localization. For example, neurons of the central portion of the ventro-caudal nucleus of the thalamus are responsive to light touch while neurons of the ventro-intermediate nucleus of the thalamus are responsive to muscle spindle activation.

Various means for applying these sensory stimulations can be used. For example, a hand held device can have a contact switch that indicates when the device touches the skin (light touch). The hand held device can also have a vibrator to stimulate muscle spindles. In a vibration mode, the contact switch indicates the time that the vibration stimuli are applied. The contact switch signal then translates to a waveform in the signal analysis logic that is then correlated with the simultaneously accumulated 4MOM indicating neuronal activity.

Joint capsule stimulation is accomplished by active and passive movement about the joint. Alternatively, an accelerometer can be attached to the physician or electrophysiologist's hand, which moves a limb about a joint as an indirect indicator of joint capsule stimulation. Such movements will be identified by small accelerometers attached to the patient's limb about the joints. The accelerometer data can be acquired and correlated with neuronal activity as described above. Optionally, a switch (foot or hand held) can be used to manually indicate stimulation or movement which cannot be directly instrumented such as a mouth opening, tongue protrusion, etc.

Figure 9:
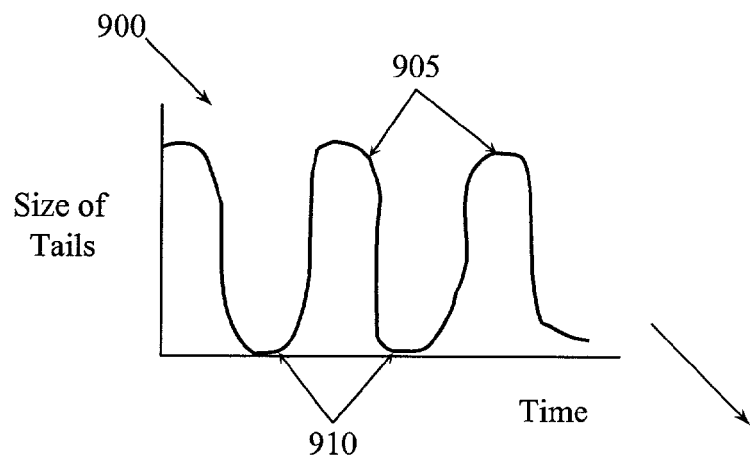
FIG. 9 is an exemplary graph of measured tail sizes of distributions generated for a plurality of time periods.

With further reference to FIG. 8, the system simultaneously records signal data as a stimulus is applied and removed. An analysis of a distribution curve's tails for each recorded epoch can be graphed as shown in FIG. 9 as graph 900. The graph shows the size of the curve's tails, where points 905 represent larger tails (indicating greater neuronal activity) and points 910 represent smaller tails (indicating little or no neuronal activity).

Figure 10:
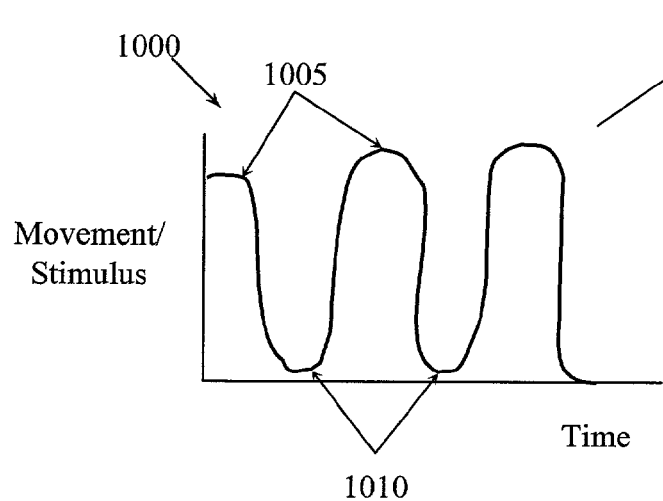
FIG. 10 is an exemplary graph measuring a stimulus or movement as applied or removed from an area over time.

FIG. 10 illustrates a graph 1000 of applied movement or stimulus corresponding in time to graph 900. Points 1005 represent when a stimulus is applied to a target and points 1010 represent no stimulus applied. With this data, the system determines if changes occur in neuronal activity (increase or decrease) based on the corresponding stimulus (block 830). The two graphs are then correlated to determine if an increase in neuronal activity corresponds to the application of stimulus (block 835). they correlate to a sufficient degree (block 840), then it is reasonable to conclude that the microelectrode recording tip is within the sensory and/or motor region of the target. If it does not correlate, then the microelectrode can be moved to a new position and the process repeats until a match is found (block 820). Alternately, the microelectrode can be maintained at its position and a new area of stimulation can be selected to determine if it correlates. It will be noted that movement of the electrode may not be tied to the identification of sensory and/or motor related units, rather it may be tied to the presence or absence of an extracellular action potential being within the signal recorded.

Figure 11:
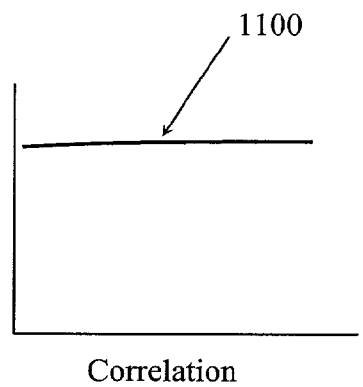
FIG. 11 is an exemplary graph showing a correlation of the data from FIGS. 9 and 10 in accordance with another embodiment of the invention.

In one embodiment, correlation can be determined using Pearson Product Moment Correlation (also called Pearson's correlation for short). Pearson's correlation reflects a degree of linear relationship between two variables. It ranges from +1 to −1. A correlation of +1 means that there is a perfect positive linear relationship between variables while a correlation of −1 means that there is a perfect negative linear relationship between variables. By correlating the data from the graphs of FIG. 9 and FIG. 10, a correlation graph is generated shown in FIG. 11. Here, there is a high correlation (positive or negative) represented by line 1100. This means that the target location of the microelectrode and the neuronal activity therein correlates or is associated with the stimulation applied. It will be appreciated that a negative correlation of sufficient degree may also demonstrate a correlation. Optionally, the system can determine the extent of a correlation by taking the absolute value of the correlation value. By using the above system, a physician can objectively determine if the microelectrode is located in a desired location based on neuronal activity.

Additionally, once a neuron action potential is located, the microelectrode can be incrementally advanced to determine the dimension of the neuronal area. Signal data is collected at each incremental location and a statistical analysis is performed to determine if it is noise or further contains neuronal activity as described above. Knowing the dimension of the neuron can help better position an implanted electrode in that location.

Data obtained and/or results found by the system can be processed for communication via the Internet or other network. Intra-operative data can be transmitted via the Internet to a central facility for processing which can assist in problem solving and data analysis and interpretation.

Thus, embodiments of the neuron analysis system and method are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A system for positioning a microelectrode within a tissue, the system comprising:
   a microelectrode for collecting electrical signals;
   a computer readable medium having:
       distribution logic that causes a computer to generate a statistical distribution of the electrical signals; and
       identification logic that that causes a computer to identify whether the statistical distribution resembles a noise distribution without neuronal discharge; and
   a position controller for controlling the position of microelectrode, the position controller moving or not moving the microelectrode based on the identification of whether the statistical distribution resembles a noise distribution without neuronal discharge.

2. The system as set forth in claim 1 wherein the statistical distribution is based on voltage amplitude values of the electrical signals.

3. The system as set forth in claim 1 wherein the noise distribution without neuronal discharge is a bell-shaped curve.

4. The system as set forth in claim 1 wherein the identification logic (i) includes logic for determining when the statistical distribution differs from the noise distribution without neuronal discharge, and (ii) generates a signal indicating possible neuron cell discharges are present in the electrical signals.

5. The system as set forth in claim 4 wherein the position controller moves the microelectrode within the brain until receipt of the signal indicating possible neuron cell discharge.

6. The system as set forth in claim 4 further including count logic for analyzing tails of the statistical distribution and indicating a quantity of neuron cell discharges in the electrical signals.

7. The system as set forth in claim 1 wherein the identification logic includes means for analyzing the statistical distribution.

8. The system as set forth in claim 1 wherein the identification logic includes logic for determining a kurtosis value of the statistical distribution.

9. The system as set forth in claim 1 further including correlation logic that correlates the statistical distribution with an applied stimulus.

10. A software product for analyzing electrical signal data collected from within tissue, the software product comprising:
   a computer readable medium including:
   logic that causes a computer to obtain electrical signal data from an microelectrode configured to be positioned within tissue;
   first computer executable instructions that cause a computer to generate a statistical distribution of the electrical signal data where the statistical distribution has a first shape which represents noise signal data without neuronal activity or a second shape that represents noise data with neuronal activity; and
   second computer executable instructions that cause a computer to analyze the statistical distribution and indicate whether neuronal activity is present in the electrical signal data based on the shape of the statistical distribution.

11. The software product as set forth in claim 10 wherein the computer readable medium further includes third computer executable instructions that cause a computer to exaggerate the electrical signal data to increase values that depart from a mean value of the statistical distribution.

12. The software product as set forth in claim 11 wherein the instructions to exaggerate include instructions that apply a fourth order moment about the mean to the electrical signal data.

13. The software product as set forth in claim 10 wherein the first shape is generally a bell shaped curve and the second shape is a curve with a departure from the bell shaped curve.

14. The software product as set forth in claim 10 wherein the statistical distribution is generated from voltage values of the electrical signal data.

15. The software product as set forth in claim 10 further including fourth computer executable instructions that cause a computer to determine an amount of neuron activity based on tails of the statistical distribution.

16. The software product as set forth in claim 10 further including fifth computer executable instructions that cause a computer to determine a kurtosis value from the statistical distribution which is used to indicate the shape of the statistical distribution.

17. The software product as set forth in claim 10 further including computer executable instructions that cause a computer to determine a correlation between neuronal activity and an applied stimulus.

18. A method of determining a nerve discharge from a plurality of electrical signals, the method comprising the steps of:
    obtaining a plurality of electrical signals via a microelectrode positioned within tissue and providing a computer to:
    statistically analyze at least one characteristic of the plurality of electrical signals and generate a distribution curve from the at least one characteristic;
    determine a statistical characteristic of the distribution curve;
    determine whether at least one nerve discharge signal occurs within the plurality of electrical signals based on the statistical characteristic of the distribution curve; and
    determine whether noise data with no neuronal discharge signal occurs within the plurality of electrical signals based on the statistical characteristic of the distribution curve; and
    provide an output indicative of whether at least one nerve discharge signal occurs or whether no neuronal discharge signal occurs.

19. The method as set forth in claim 18 further including:
    automatically moving the electrode to a different location and collecting another set of electrical signals when the statistical characteristic of the distribution curve represents a noise distribution without a neuronal discharge signal.

20. The method as set forth in claim 18 wherein the distribution curve is generated from voltage values of each of the plurality of electrical signals.

21. The method as set forth in claim 18 further including collecting the plurality of electrical signals over a predetermined time period.

22. The method as set forth in claim 18 wherein the statistically analyzing step includes generating a generally bell-shaped distribution curve when the plurality of electrical signals represent noise signals without neuronal activity, and generating a distribution curve different from the generally bell-shaped distribution curve when the plurality of electrical signals contain neuronal activity.

23. The method as set forth in claim 18 wherein the step of determining a statistical characteristic includes:
    determining a central tendency of the plurality of electrical signals; and
    measuring an amount of signal dispersion from the central tendency.

24. The method as set forth in claim 18 further including determining an amount of nerve discharge signals within the plurality of electrical signals by a size of a tail of the distribution curve.

25. The method as set forth in claim 18 further including determining whether at least one nerve discharge signal occurs within the electrical signal data simultaneously with an applied stimulation.

26. The method as set forth in claim 18 wherein the step of determining a statistical characteristic of the distribution curve includes determining a kurtosis value from the distribution curve.

27. The method as set forth in claim 18 wherein the step of determining a statistical characteristic of the distribution curve includes determining a size of tails of the distribution curve.

28. The method as set forth in claim 18 wherein the step of determining a statistical characteristic of the distribution curve includes determining a plurality of statistical characteristics.

29. A device for analyzing electrical signal data collected from tissue, the device comprising:
    a microelectrode adapted to be positioned in a tissue for collecting electrical signal data;
    computer readable medium containing first computer executable instructions that cause a computer to generate a statistical distribution of the electrical signal data wherein the statistical distribution is one selected from a first shape which represents noise signal data without neuronal activity and a second shape that represents noise signal data with neuronal activity;
    computer readable medium containing second computer executable instructions that cause a computer to analyze the statistical distribution and indicate whether neuronal activity is present in the electrical signal data based on the shape of the statistical distribution; and
    an indicator for controlling the position of the microelectrode, the indicator issuing commands for moving or not moving the microelectrode based on the shape of the statistical distribution.

30. The device as set forth in claim 29 further including third computer executable instructions that cause a computer to exaggerate the electrical signal data to increase values that depart from a mean value of the statistical distribution.

31. The device as set forth in claim 30 wherein the instructions to exaggerate include instructions that apply a fourth order moment about the mean to the electrical signal data.

32. The device as set forth in claim 29 wherein the first shape is generally a bell shaped curve and the second shape is a curve with a departure from the bell shaped curve.

33. The device as set forth in claim 29 wherein the statistical distribution is generated from voltage values of the electrical signal data.

34. The device as set forth in claim 29 wherein the computer readable medium further include fourth computer executable instructions that cause a computer to determine an amount of neuron activity based on tails of the statistical distribution.

35. The device as set forth in claim 29 wherein the computer readable medium further include fifth computer executable instructions that cause a computer to determine a kurtosis value from the statistical distribution which is used to indicate the shape of the statistical distribution.

36. The device as set forth in claim 29 wherein the computer readable medium further include computer executable instructions that cause a computer to determine a correlation between neuronal activity and an applied stimulus.

37. A method of determining one or more nerve discharge signals from a plurality of electrical signals, the method comprising the steps of:
   obtaining a plurality of electrical signals from a microelectrode positioned within tissue and providing computer to:
   statistically analyze at least one characteristic of the plurality of electrical signals and generating a distribution curve from at least one characteristic;
   determine a statistical characteristic of the distribution curve;
   determine whether at least one nerve discharge signals occurs within the plurality of electrical signals based on the statistical characteristic of the distribution curve;
   determine whether no neuronal discharge signal occurs within the plurality of electrical signals based on the statistical characteristic of the distribution curve; and
   provide an output indicative of whether at least one nerve discharge signal occurs or whether no neuronal discharge signal occurs.

38. The method as set forth in claim 37 wherein the distribution curve is generated from voltage values of each of the plurality of electrical signals.

39. The method as set forth in claim 37 further including providing the computer to collect the plurality of electrical signals over a predetermined time period.

40. The method as set forth in claim 37 wherein the statistically analyzing step includes providing the computer to generate a generally bell-shaped distribution curve when the plurality of electrical signals represent noise signals without neuronal activity, and generating a distribution curve different from the generally bell-shaped distribution curve when the plurality of electrical signals contain neuronal activity.

41. The method as set forth in claim 37 wherein the step of determining a statistical characteristic includes:
   determining a central tendency of the plurality of electrical signals; and
   measuring an amount of signal dispersion from the central tendency.

42. The method as set forth in claim 37 further including providing the computer to determine an amount of nerve discharge signals within the plurality of electrical signals by a size of a tail of the distribution curve.

43. The method as set forth in claim 37 wherein the step of determining a statistical characteristic of the distribution curve includes determining a kurtosis value from the distribution curve.

44. The method as set forth in claim 37 wherein the step of determining a statistical characteristic of the distribution curve includes determining a size of tails of the distribution curve.

* * * * *

UNITED STATES PATENT AND TRADEMARK OFFICE
CERTIFICATE OF CORRECTION

| | | |
|---|---|---|
| PATENT NO. | : 7,136,696 B2 | Page 1 of 1 |
| APPLICATION NO. | : 10/138987 | |
| DATED | : November 14, 2006 | |
| INVENTOR(S) | : Erwin B. Montogomery, Jr. | |

It is certified that error appears in the above-identified patent and that said Letters Patent is hereby corrected as shown below:

Column 10, line 11, claim 1, delete second occurence "that".
Column 10, line 53, claim 10, "an" should be changed to --a--.
Column 12, line 64, claim 34, "include" should be changed to --includes--.
Column 13, line 2, claim 35; and column 13, line 7, claim 36, "include" should be changed to --includes--.

Signed and Sealed this

Fifteenth Day of May, 2007

JON W. DUDAS
*Director of the United States Patent and Trademark Office*